United States Patent [19]
Morgan et al.

[11] Patent Number: 6,132,716
[45] Date of Patent: *Oct. 17, 2000

[54] **THERMOSTABLE XYLANASES FROM *MICROTETRASPORA FLEXUOSA* AS A FEED ADDITIVE**

[75] Inventors: Andrew J. Morgan, Marlborough, United Kingdom; Kathleen A. Clarkson, San Francisco, Calif.; Elizabeth A. Bodie, Belmont, Calif.; William A. Cuevas, San Francisco, Calif.

[73] Assignee: Genencor International, Inc., Rochester, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/732,242
[22] PCT Filed: Apr. 28, 1995
[86] PCT No.: PCT/EP95/01628
  § 371 Date: Apr. 7, 1997
  § 102(e) Date: Apr. 7, 1997
[87] PCT Pub. No.: WO95/29997
  PCT Pub. Date: Nov. 9, 1995

Related U.S. Application Data

[63] Continuation-in-part of application No. 08/234,338, Apr. 28, 1994, Pat. No. 5,437,992.
[51] Int. Cl.[7] .......................... A61K 38/47; A23K 1/165; A23L 1/28; C12N 9/24
[52] U.S. Cl. .................. 424/94.61; 424/438; 424/442; 426/53; 426/54; 426/61; 426/635; 426/807; 435/200; 435/252.1; 435/822
[58] Field of Search .................. 435/195, 200, 435/252.1, 822; 424/94.61, 438, 442; 426/42, 52, 53, 61, 635, 807

[56] References Cited

U.S. PATENT DOCUMENTS

| 5,395,765 | 3/1995 | Dahlberg et al. | 435/277 |
| 5,437,992 | 8/1995 | Bodie et al. | 435/200 |
| 5,683,911 | 11/1997 | Bodie et al. | 435/201 |

OTHER PUBLICATIONS

Irwin, et al., Microbiology, vol. 60, No. 3, Mar. 1994, pp. 763–770.

*Primary Examiner*—David M. Naff
*Attorney, Agent, or Firm*—Lynn Marcus-Wyner; Genencor International, Inc.

[57] ABSTRACT

A feed additive that provides increased feed conversion ratio is prepared containing a physiologically acceptable carrier and one or more of five thermostable xylanases from *Microtetraspora flexuosa*, preferably strain ATCC 35864. The xylanases can tolerate heating for one minute in a water bath at 95° C. without substantial loss of activity, and tolerate alkaline conditions in a pH range of 7.0–10.0. A feed for poultry or pigs contains the xylanases in a feed containing at least 20% by weight cereal. The five xylanases have the following characteristics: (i) a molecular weight of about 33,100 daltons, a pI of about 8.5, and a maximum activity at pH 7.0–7.5 at a temperature of about 70° C.; (ii) a molecular weight of about 33,300 daltons, a pI of about 7.5, and a maximum activity at pH 7.0–7.5 at a temperature of about 65° C.; (iii) a molecular weight of about 31,000 daltons, a pI of about 6.2, and a maximum activity at pH 7.5 at a temperature of about 65° C.; (iv) a molecular weight of about 50,000 daltons, a pI of about 5.8, and a maximum activity at pH 7.5 at a temperature of about 65° C.; and (v) a molecular weight of about 35,000 daltons, a pI of about 5.3, and a maximum activity at pH 7.5 at a temperature of about 70° C.

7 Claims, 3 Drawing Sheets

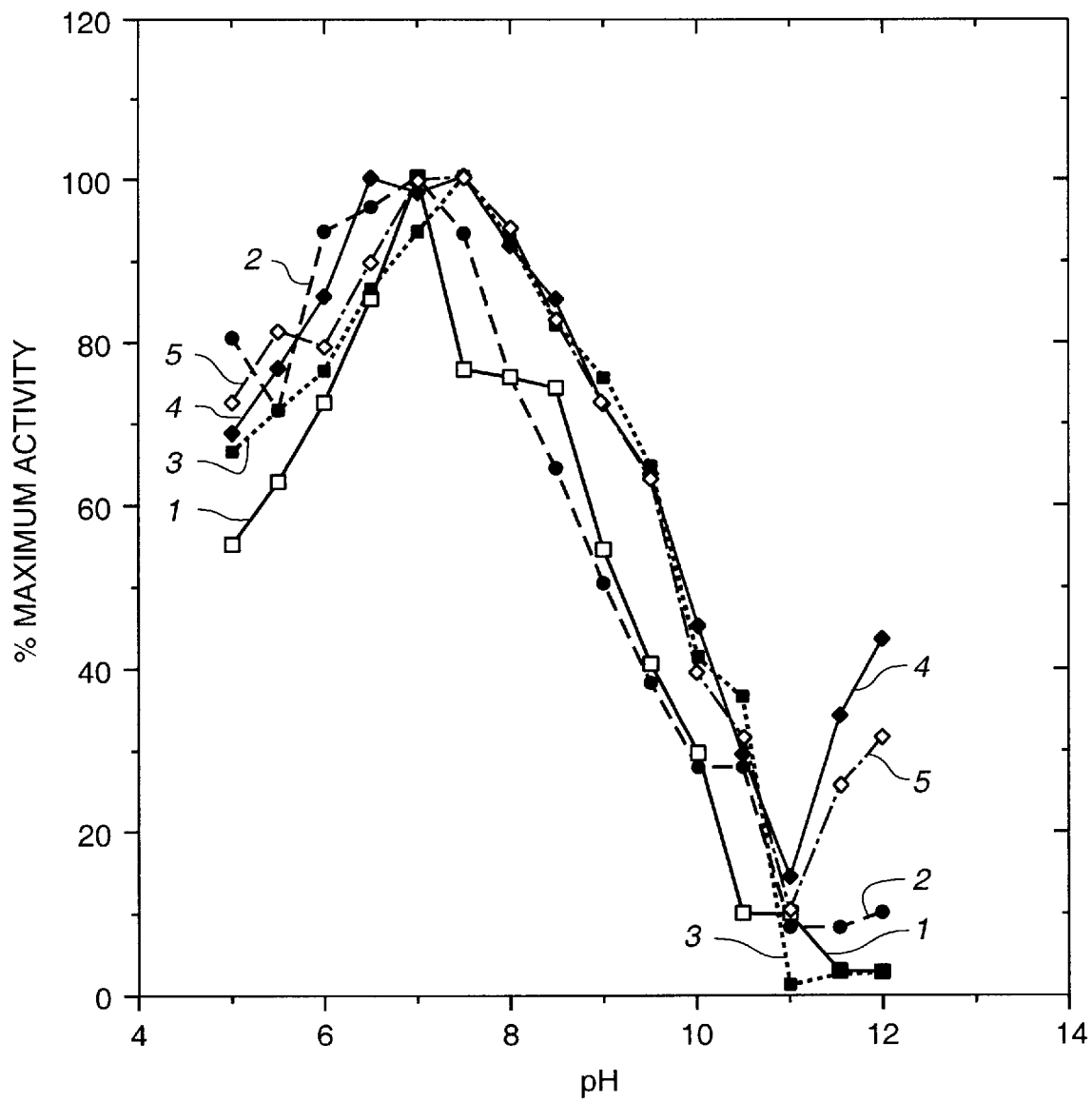
FIG._1

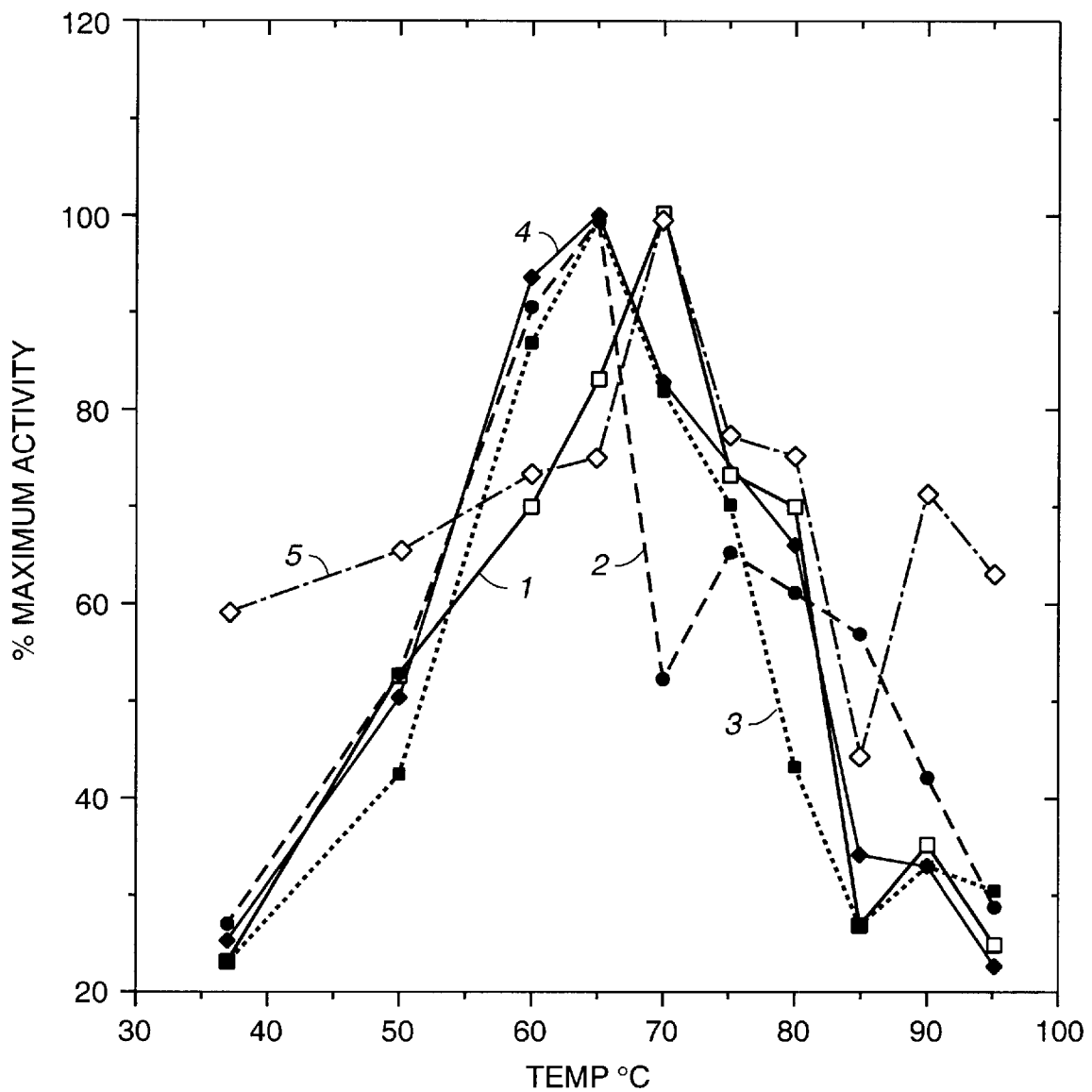
FIG._2

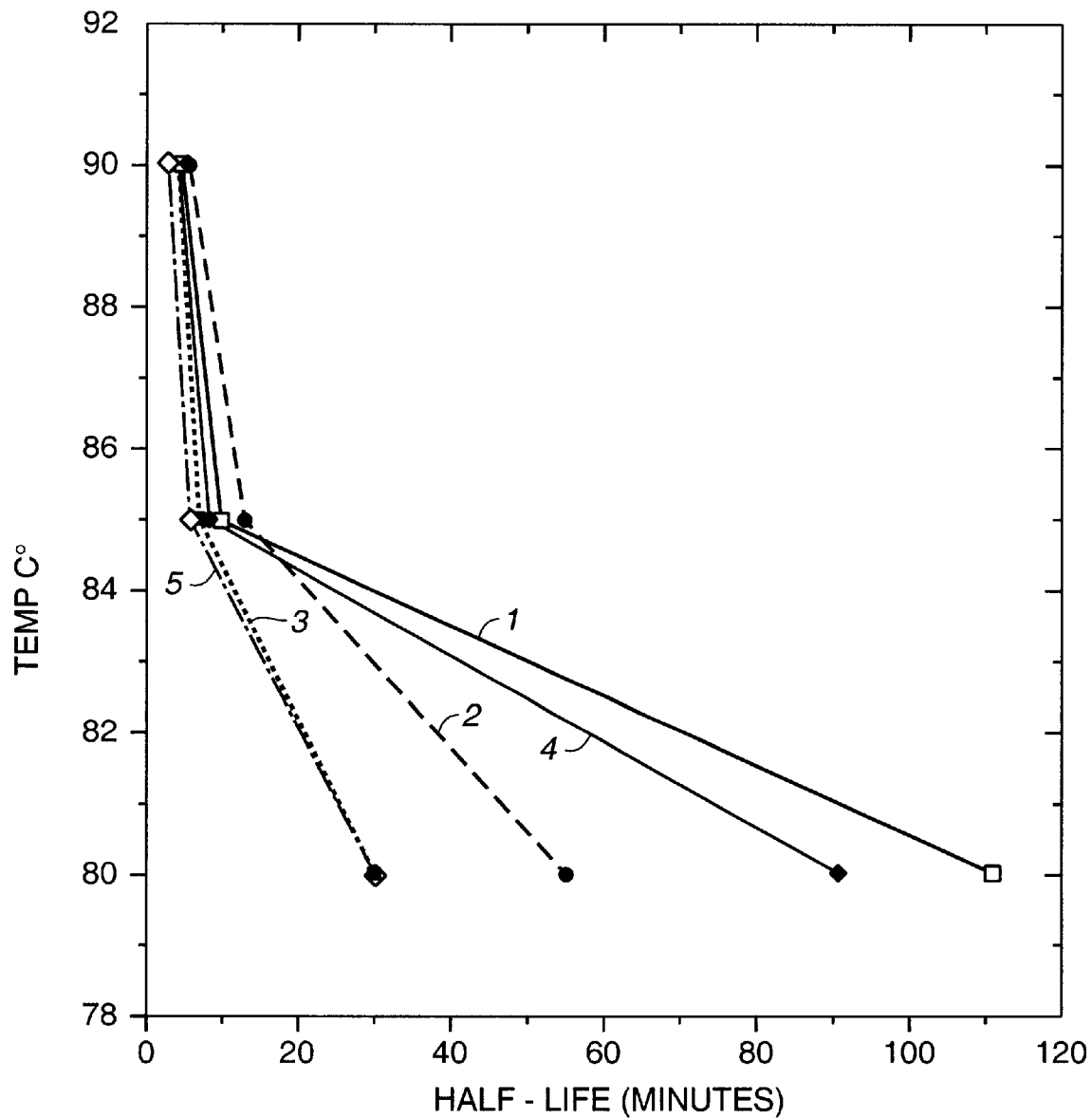
FIG._3

THERMOSTABLE XYLANASES FROM *MICROTETRASPORA FLEXUOSA* AS A FEED ADDITIVE

CROSS-REFERENCE TO RELATED APPLICATIONS

This patent application is a continuation-in-part of application Ser. No. 08/234,338, filed Apr. 28, 1994, now U.S. Pat. No. 5,437,992, which is a national filing of international patent application PCT/EP95/01628.

FIELD OF THE INVENTION

The present invention relates to the use of an enzyme as an additive for an animal feed, and in particular to such a use where the enzyme is thermostable so that it does not suffer a significant decline of its activity during relatively high temperature feed processing. The invention also provides a feed additive and a cereal-based feed including such a thermostable enzyme.

BACKGROUND OF THE INVENTION

Improvements in animal feeds to enable animals to digest the feeds more efficiently are constantly being sought. One of the main concerns is to improve the Feed Conversion Ratio (FCR) of a feed without increasing its cost per unit weight. The FCR of a feed is the ratio of the amount of feed consumed relative to the weight gain of the animal. A low FCR indicates that a given amount of feed results in a growing animal gaining proportionately more weight. This means that the animal is able to utilise the feed more efficiently. One way in which the FCR can be reduced is to improve its digestibility by an animal thereby increasing the nutritional benefit which the animal can derive from it.

There are various constraints on the digestibility of the nutritional components of a feed such as its starch, fat, protein and amino acid content. These constraints include:

(i) the viscosity of materials present in the animal's gut. Such viscosity is due, at least in part, to soluble non-starch polysaccharides such as mixed-linked β-glucans and arabinoxylans;

(ii) entrapment of nutrients within the cell walls of the feed, particularly those of the aleurone layer in cereals. Such entrapment is caused by the high levels of non-starch polysaccharides in the cell walls of cereals which are relatively resistant to break-down by the animal's digestive system. This prevents the nutrients entrapped within the cells from being nutritionally available to the animal; and (iii) a deficiency in endogenous enzyme activity, both of the animal and of the gut microbial population particularly in a young animal.

The above problems which interfere with digestibility are particularly noticeable in the case of cereal-based diets, such as those having a high wheat content.

Due to the problem of poor digestibility of nutrients from the feed, it is normally necessary to formulate feeds to contain higher levels of energy and protein providing materials in order to meet the nutritional demands of animals.

There is now a substantial body of evidence that incorporating certain (supplementary) enzymes in cereal-based animal feeds can be advantageous in reducing the viscosity of material present in the animal's gut. This reduction can be achieved by enzymes such as xylanases which hydrolyse soluble xylans thereby reducing digesta viscosity which is an important constraint on the process of digestion.

The xylanases which are added as supplements must be stable and active at the pH and temperature conditions found within the gastrointestinal (GI) tract of the target animal. If they are not stable and active when exposed to such in vivo conditions, then they will not be able to reduce digesta viscosity to any significant extent. It is presently known to include xylanases as a supplement in an animal feed derived from fungi such as *Trichoderma longibrachiatum*, *Aspergillus niger* and *Humicola insolens*.

Bedford and Classen (The Journal of Nutrition, vol. 122, pp 560–569) disclose that there is a significant correlation between digesta viscosity measured in vivo in the case of broiler chickens and bodyweight gain and FCR values. In the case of wheat and rye-based diets fed to poultry, it was shown that as much as 70–80% of the variations in the weight gain and FCR are based upon differences in intestinal viscosity alone. This highlights the importance of digesta viscosity in cereal-based feeds containing high levels of soluble arabinoxylans. As digesta viscosity increases, it reduces the digestibility of all nutrients by interfering with the diffusion of pancreatic enzymes, substrates and the end products of the digestion process.

It has been found that the inclusion of a xylanase in an animal feed helps to reduce the digesta viscosity in livestock. As a result of this, the animal's ability to digest the feed is increased, the rate of bodyweight gain of the animal per unit amount of feed consumed is increased, and the FCR of the feed is decreased.

It is conventional to include enzyme supplements, such as xylanase, in an animal feed by impregnating the enzyme onto a physiologically acceptable carrier, such as a cereal. The impregnated carrier is mixed with the other components of the feed and then pressed into cubes or pellets for feeding directly to animals.

There has recently been much development in the processing of the various feed components into forms such as cubes and pellets. The processes which have been developed make use of relatively high temperatures. This is firstly to improve the efficiency of the manufacturing process and secondly to produce feeds which are free from harmful bacteria, particularly Salmonella. In addition, the use of high temperatures improves the quality and durability of the resulting cubes and pellets, increases the range of ingredients which can be efficiently handled and also increases the level of liquid ingredients, such as fat and molasses, which can be incorporated into the feed.

The processing techniques currently employed apply relatively high temperatures to the mixture of feed components for a relatively long period. Further, the mixture is subjected to relatively high pressures during processing which also helps to increase the durability of the cubes or pellets formed.

One of the processing methods which has been developed to improve the nutritional properties of the feed is steam pelleting. This method includes the step of treating the compounded feed with steam to increase its temperature and moisture content. This step is termed conditioning. Conditioning lasts from a few seconds up to several minutes depending on the type and formulation of the feed. The temperature in the conditioner may rise to 100° C. Afterwards, the feed is passed through a pelleting die which causes a rapid increase in its temperature due to friction.

Recently, a new device for pre-treatment or conditioning of feeds has been introduced called an expander. This allows sustained conditioning under pressure followed by pelleting. According to this technique, various feed components which have previously been subjected to steam-conditioning are fed into a compression screw into which more steam is injected, and the mass is then subjected to increasing pressure and shear action and then forced through a variable exit gap. The compressed product, after reduction in particle size, is fed into a standard pelleting press.

The dwell time of the feed components in the expander is about 5–20 seconds, and the temperature reached may be as high as 145° C. A compression pressure of about 3.5 MPa is reached, but the build-up of both temperature and pressure is very quick and both fall rapidly as the product is expelled through the exit gap.

The use of expanders is advantageous because they effectively eliminate harmful bacteria, particularly Salmonella. Furthermore, it is possible to include relatively high levels of fat and other liquid ingredients in the mixture prior to pelleting. In addition, the cooking and pressure/shear action results in greater starch gelatinisation.

Unfortunately, these high temperature and high pressure processing conditions, particularly when applied in the moist conditions normally encountered during pelleting, are potentially destructive to certain feed components. This is particularly true of any enzymes, including xylanases, which are present.

As is well known, enzymes are proteins, and thus are made up of amino acids. The particular sequence of amino acids, the "primary structure", determines the nature of the protein. The amino acid chain may then be arranged in a number of "secondary structures" such as sheets and helices. These structures are also organised in relation to each other to give a "tertiary structure"; for example the sheets may lie parallel to each other, rather like the pages of a newspaper. Lastly, several sub-units may be associated together in a particular enzyme, and this gives rise to "quaternary structure".

To function, an enzyme must possess an active site which is capable of catalysing the reaction of a particular substrate. This active site often has a very specific shape, which is determined by the primary, secondary, tertiary and quaternary structures of the enzyme. Changes in the shape of the catalytic site are likely to deactivate the enzyme.

There are several factors, including heat, pressure and pH, which may alter the shape of an enzyme and so also its active site. During feed processing, any enzyme already present in the mixture will be subjected to temperatures and pressures which may well cause the enzyme to at least partially denature and thus lose some or all of its activity. The higher the temperature to which an enzyme is exposed during processing, the greater its activity will decline. Typically, mesophilic xylanases are stable at temperatures up to 65° C. but lose all activity if exposed to a temperature of 95° C. at least in an aqueous solution.

If such temperature mediated denaturing occurs during feed processing, it is of course extremely disadvantageous as then the enzyme will not give rise to the effect for which it was added, or will only give rise to such an effect to a limited extent. One possibility of overcoming this problem would be to include significantly greater relative amounts of the enzyme to the feed in order to compensate for the deactivation of a certain proportion. However, adding such additional amounts is disadvantageous from an economic viewpoint because the enzymes which are incorporated in animal feeds are relatively expensive.

It has also been investigated to stabilise the enzymes by coating them on special carriers or by coating them using specialised coating technologies. However, methods such as these have not been able to deal effectively with the relatively severe processing conditions encountered in high temperature steam pelleting, in an expander or in an extruder.

An alternative solution would be to add enzymes, such as xylanase, to pre-formed pellets which have already been heat treated. This however is not an ideal solution because firstly complex and expensive machinery is required to precision coat the enzyme on the pellets to achieve the desired relative amount of inclusion.

Secondly, the solutions of enzymes which are used in such a coating procedure have limited storage stability and can become contaminated by bacteria.

Accordingly, even though partial solutions to the problem of enzyme stability during feed processing are available, none of them solves the problem in a totally effective manner.

In the description and claims which follow, reference is made to units of xylanase activity. This activity as used in the present invention is measured by the following assay method.

SUMMARY OF THE INVENTION

In accordance with one aspect, the present invention is directed to an enzyme feed additive comprising a physiologically acceptable carrier and one or more xylanases obtained from *Microtetraspora flexuosa* and possessing one or more of the following characteristics (i)–(v): (i) a molecular weight of about 33,100 daltons, a pI of about 8.5, and having a maximum activity at a pH in the range 7.0–7.5 and at a temperature of about 70° C.; (ii) a molecular weight of about 13,300 daltons, a pI of about 7.5, and having a maximum activity at a pH in the range 7.0–7.5 and at a temperature of about 65° C.; (iii) a molecular weight of about 31,000 daltons, a pI of about 6.2, and having a maximum activity at a pH of about 7.5 and at a temperature of about 65° C.; (iv) a molecular weight of about 50,000 daltons, a pI of about 5.8, and having a maximum activity at a pH of about 7.5 and at a temperature of about 65° C.; and (v) a molecular weight of about 35,000 daltons, a pI of about 5.3, and having a maximum activity at a pH of about 7.5 and at a temperature of about 70° C. In accordance with a second aspect of the present invention, the enzyme feed additive is used in a method for improving the feed conversion ratio of a cereal-based feed.

In accordance with another aspect, the invention is directed to a cereal-based feed comprising at least 20% by weight of cereal and 0.00001–10 g of thermostable xylanase protein per kilogram of feed, the thermostable xylanase comprising one or more xylanases obtained from *Microtetraspora flexuosa* and possessing one or more of the characteristics (i)–(v) as described above. In yet a further aspect, the present invention is directed to a method of preparing an animal feed for poultry or pigs comprising the cereal-based feed as herein disclosed.

BRIEF DESCRIPTION OF THE DRAWINGS

FIG. 1 depicts the activity pH profile of the five purified xylanases from *Microtetraspora flexuosa*.

FIG. 2 depicts the activity temperature profile of the five purified xylanases from *Microtetraspora flexuosa*.

FIG. 3 shows the temperature stability profile of the five purified xylanases from *Microtetraspora flexuosa*.

DETAILED DESCRIPTION OF THE PREFERRED EMBODIMENTS OF THE INVENTION

Assay Method for Xylanase Activity

One unit of xylanase activity is the amount of enzyme which liberates one $\mu$mol of reducing sugars (expressed as xylose equivalents), from the substrate in one minute under the conditions described.

Reagents 1. 1% (w/v) xylan substrate

Add 10 ml of 0.5 M sodium hydroxide to 1.0 g of xylan (Fluka 95590). Mix for 30 minutes with a magnetic stirrer. Add about 40 ml of 0.05 M sodium acetate buffer, pH 6.5. Adjust pH to 6.5 with 1 M acetic acid. Fill to 100 ml with 0.05 M sodium acetate buffer, pH 6.5. Substrate should be mixed all the time when used.

2. 1 M acetic acid

Pipette 5.7 ml of glacial acetic acid into a volumetric flask and fill to 100 ml with distilled water.

3. 0.05 M sodium acetate buffer, pH 6.5

A. Dissolve 4.1 g of sodium acetate in distilled water and fill to 1000 ml with distilled water.

B. Dissolve 3.0 g of glacial acetic acid in distilled water and fill to 1000 ml with distilled water.

Adjust the pH of solution A to pH 6.5 with solution B.

4. Dinitrosalicylic acid (DNS) reagent

Suspend 20.0 g of 3,5-dinitrosalicylic acid in about 800 ml of distilled water. Add gradually 300 ml of sodium hydroxide solution (32.0 g NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until the solution is clear.

Fill to 2000 ml with distilled water and filter through a coarse sintered glass filter.

Store in a dark bottle at room temperature. The Reagent is stable for a maximum of 6 months.

Procedure

1. Enzyme sample 1 ml of enzyme dilution (in 0.05 M sodium acetate buffer, pH 6.5) is equilibrated at +50° C. Add 1 ml of xylan substrate, stir and incubate at +50° C. for exactly 30 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme blank

Incubate 1 ml of xylan substrate at +50° C. for 30 minutes Add 3 ml of DNS-solution and stir. Add 1 ml of enzyme dilution (in 0.05 M sodium acetate buffer, pH 6.5) and stir. Boil the mixture for exactly 5 minutes. Cool the reaction mixture in a cold water bath to room temperature and measure the absorbance at 540 nm against distilled water.

The absorbance difference between the enzyme sample and enzyme blank should be 0.3–0.5.

3. Standard curve

Prepare standard solutions from anhydrous xylose in 0.05 M sodium acetate buffer, pH 6.5. Xylose concentration in the standards should be 0.05–0.5 mg/ml. Pipette 1 ml of standard solution, 1 ml of xylan substrate and 3 ml of DNS-reagent into a test tube. Stir and boil for exactly 5 minutes. Cool in a cold water bath to room temperature and measure the absorbance at 540 nm against standard blank. In the standard blank, xylose solution is replaced by 1 ml of 0.05 M sodium acetate buffer, pH 6.5. Otherwise standard blank is treated like xylose standard.

Plot xylose concentration as a function of absorbance. New standard curve is prepared for every new DNS-reagent.

Calculation

The xylanase activity of the sample is calculated according to the following equation:

$$\text{Activity (U/g)} = \frac{([A(x) - A(0)] \times k + C.) \times 1000 \times Df}{MW_{xyl} \times t}$$

wherein:

$A(X)$=absorbance of the enzyme sample
$A(O)$=absorbance of the enzyme blank
k=the slope of the standard curve
C=the intercept of xylose standard curve
1000=factor, mmol→$\mu$mol
Df=dilution factor (ml/g)
$MW_{xyl}$=molecular weight of xylose (156.13 mg/mmol)
t=reaction time (30 minutes)

Based upon the above considerations, it is one object of the present invention to provide a xylanase as an additive for an animal feed which retains substantially all of its activity when subjected to processing techniques which expose it to relatively high temperatures.

Accordingly, the present invention provides the use of a thermostable xylanase obtainable from *Microtetraspora flexuosa* as an additive for an animal feed, the xylanase being characterised by being able to tolerate heating for one minute in a water-bath set at 95° C. without substantial loss of activity as determined by its ability to reduce the viscosity of a 1% wheat arabinoxylan solution at pH 6.5 and at a temperature of 40° C. to the same final viscosity, ±0.001 Pascal seconds, as an unheated control.

Preferably, the xylanase is able to reduce the viscosity of a 1% wheat arabinoxylan solution at pH 6.5 and at a temperature of 40° C. to the same final viscosity, ±0.0005 Pascal seconds, as an unheated control.

The assay for xylanase activity outlined above is an in vitro viscosity-reducing assay using wheat arabinoxylan as a viscous substrate under conditions which mimic those found in the GI tract of an animal. Such an in vitro assay acts as a guide as to whether a xylanase (or mixture of xylanases) would have the desired effect of reducing digesta viscosity if used as a supplement in an animal feed.

Full details of the viscosity-reducing assay used to measure the ability of a xylanase to reduce viscosity are as follows. The assay is carried out in all cases in duplicate.

The xylanase enzyme to be assayed is diluted with 0.1 M Na-phosphate buffer having a pH of 6.5 in order to adjust the xylanase concentration so that the resulting solution possesses a xylanase activity of 1.0 unit per ml. Such xylanase activity is determined according to the assay method for xylanase activity described in detail above.

100 $\mu$l of the enzyme solution was added to 400 $\mu$l of a solution of wheat arabinoxylan (obtained from Megazyme Pty) in 0.1 M Na-phosphate at pH 6.5 in a glass test tube so that the final concentration of enzyme in the resulting solution was 0.2 U/ml and that of the wheat arabinoxylan was 1.0% w/w.

The test tubes containing the solutions were then sealed and placed in a water-bath set at 95° C. for a certain period of time, typically 1 minute or 5 minutes. After this heat treatment, the test tubes were cooled in an ice-water bath. The viscosity of the resulting solution was measured after 20 minutes at a temperature of 40° C. using a Brookfield DV-II, CP 40 viscometer programmed to measure viscosity once a second.

The use of the thermostable xylanase as an additive for an animal feed according to the present invention has the advantage that the activity of the xylanase is not substantially reduced after it is combined with the other feed components and subjected to conventional feed processing using for instance an expander or an extruder.

The thermostable xylanase for use in the present invention is obtainable from *Microtetraspora flexuosa*.

The isolation of thermostable xylanases from *Microtetraspora flexuosa* is described in detail below. It has been found that five different thermostable xylanases can be isolated from *Microtetraspora flexuosa*. These xylanases are referred to below as xylanases 1–5 respectively. These xylanases have been purified to homogeneity as measured by silver staining isoelectric focusing gels. The xylanases have been purified by a combination of ion-exchange chromatography and hydrophobic interaction chromatography. Each purified xylanase is characterised as being thermostable over a wide pH range. Specifically, each xylanase retains greater than 80% activity in the pH range of 6–9.

The xylanases may be further characterised as follows. Xylanase 1 has a molecular weight of about 33,100 daltons, a pI of about 8.5, and has a maximum activity at a pH in the range 7.0–7.5 and at a temperature of 70° C. Xylanase 2 has a molecular weight of about 13,300 daltons, a pI of about 7.5, and has a maximum activity at a pH in the range 7.0–7.5 and at a temperature of about 65° C. Xylanase 3 has a molecular weight of about 31,000 daltons, a pI of about 6.2, and has a maximum activity at a pH of about 7.5 and at a temperature of about 65° C. Xylanase 4 has a molecular weight of about 50,000 daltons, a pI of about 5.8, and has a maximum activity at a pH of about 7.5 and at a temperature of about 65° C. Xylanase 5 has a molecular weight of about 35,000 daltons, a pI of about 5.3, and has a maximum activity at a pH of about 7.5 and at a temperature of about 70° C.

The xylanases of *Microtetraspora flexuosa* can be used in accordance with the present invention either as a mixture of all five of the xylanases, that is as a whole xylanase supernatant, individually, or as any combination thereof. An alternative way of preparing the xylanase for use in the present invention is to construct by recombinant DNA techniques an appropriate host microorganism which produces the desired thermostable xylanase. Thus the xylanase may be obtained from a host which has been subjected to genetic manipulation such as by the inclusion of a gene from *Microtetraspora flexuosa* encoding a thermostable xylanase within a host bacterial or fungal strain.

The xylanases 1–5 obtained from *Microtetraspora flexuosa* can be derived from the strain deposited as ATCC 35864 at the American Type Culture Collection, Manassas, Va., U.S.A. from where the strain is readily available. The isolation of the novel xylanases involves the purification of the extracellular xylanases by a combination of ion-exchange chromatography (IEC) and hydrophobic interaction chromatography (HIC) in either order depending on the xylanase to be purified.

The two purification methods to isolate and characterise the five chemically distinct xylanases derived from *Microtetraspora flexuosa* are as follows. In both methods, *Microtetraspora flexuosa* cells are removed by centrifugation and the culture broth is concentrated using ultrafiltration. In the first method, xylanase 1 (pI 8.5), xylanase 2 (pI 7.5), and xylanase 4 (pI 5.8) are separated and purified. The cell free whole culture broth preparation is applied to an anion-exchange column, washed and diluted with an increasing salt (NaCl) gradient. After the fractions are collected, xylanase activity is measured using a remazol brilliant blue dyed birchwood xylan assay (RBB-xylan assay). Xylanase 1 and xylanase 2 elute in the column breakthrough. The effluent breakthrough is pooled and reloaded onto a hydrophobic interaction column (phenyl Sepharose). Xylanase 1 and xylanase 2 separate from each other by eluting the column with increasing concentrations of ethylene glycol. Xylanase 4 binds to the anion exchange column and elutes in the salt gradient with the other bound xylanases (xylanases 3 and 5). Xylanase 4 was separated from the other xylanases by HIC. This is more fully described in Example 1 below. Purified xylanases 1, 2 and 4 were further analysed by isoelectric focusing and mass spectrophotometry (MS) or sodium dodecyl sulphate polyacrylamide gel electrophoresis (SDS-PAGE).

In the second method, the cell free whole culture broth described above was subjected to HIC as a first step to purify xylanase 3 (pI 6.2) and xylanase 5 (pI 5.3). Both xylanases co-elute at the same concentration of ammonium sulphate. To separate xylanase 3 and xylanase 5 from each other, IEC was performed on the pooled eluted active enzyme materials. Xylanase 3 elutes from an anion-exchange column at a lower salt concentration than xylanase 5. Both purified xylanases were first characterised by isoelectric focusing and MS or SDS-PAGE.

Each xylanase has been distinguished from the others by its unique biochemical characteristics, e.g. molecular weight, pI, optimum temperature and pH, hydrophobic properties and temperature stability. All five xylanases can tolerate high temperatures of up to 90° C. and alkaline conditions within the range pH 7.0–10.0. The five purified xylanases have a half-life at 80° C. ranging from 30 minutes to 110 minutes. A further characterisation of each of the five xylanases purified to homogeneity is described in Reference Example 2 below.

According to a further aspect of the present invention, there is provided a feed additive comprising a physiologically acceptable carrier and a thermostable xylanase obtainable from *Microtetraspora flexuosa*, the xylanase being characterised by being able to tolerate heating for one minute in a water-bath set at 95° C. without substantial loss of activity as determined by its ability to reduce the viscosity of a 1% wheat arabinoxylan solution at pH 6.5 and at a temperature of 40° C. to the same final viscosity, ±0.001 Pascal seconds, as an unheated control.

According to this aspect, the thermostable xylanase may be any one or any mixture of the xylanases previously described.

The physiologically acceptable carrier in this aspect of the present invention is preferably a cereal or derived from a cereal. Such cereals include milled wheat, maize, soya, sugars, starches or a by-product of any of these. Such carriers are conventional in this technical art, and so are not described in any further detail.

The feed additive according to this aspect of the present invention is combined with other feed components to produce a cereal-based feed. Such other feed components include one or more other (preferably thermostable) enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using any of the currently used processing apparatuses such as a double-pelleting machine, a steam pelleter, an expander or an extruder.

The presence of the thermostable xylanase in the resulting cereal-based feed has the effect of reducing its FCR. The xylanase may alternatively or additionally increase the digestibility of the cereal-based feed. Further the inclusion of the xylanase may additionally or alternatively increase the rate of bodyweight gain in an animal per unit amount of feed which the animal consumes.

The present invention provides in a further aspect, a cereal-based feed comprising at least 20% by weight of cereal, and 0.00001 g–10 g of thermostable xylanase protein per kg of feed, the xylanase being obtainable from *Microtetraspora flexuosa*, and being characterised by being able to tolerate heating for one minute in a water-bath set at 95° C. without substantial loss of activity as determined by its ability to reduce the viscosity of a 1% wheat arabinoxylan solution at pH 6.5 and at a temperature of 40° C. to the same final viscosity, ±0.001 Pascal seconds, as an unheated control.

In this aspect of the present invention, the thermostable xylanase may again be any one or any mixture of the thermostable xylanases previously described. In such a cereal-based feed, the cereal is preferably at least one of wheat, barley, maize, sorghum, rye, oats, triticale and rice. It is particularly preferred that the cereal should be wheat.

The cereal-based feed according to the present invention may be provided to animals such as turkeys, geese, ducks, sheep and cows. It is however particularly preferred that the feed is provided to pigs or to poultry, and in particular broiler chickens.

The cereal-based feed preferably includes 0.0001–1 g of xylanase protein per kilo of the feed; and most preferably 0.001–0.1 g/kg.

The cereal-based feed comprises at least 20% by weight of cereal. More preferably, it should include at least 30% by weight of the cereal, and most preferably at least 50% by weight of the cereal. The cereal can be any of those previously mentioned, with wheat being particularly preferred.

Although the cereal component of a cereal-based feed constitutes a source of protein, it is usually necessary to include sources of supplementary protein in the feed such as those derived from fish-meal, meat-meal or vegetables. Sources of vegetable proteins include at least one of full fat soybeans, rapeseeds, canola, soybean-meal, rapeseed-meal and canola-meal. As compared to conventional feeds, the relative amount of the additional protein sources such as fish-meal, meat-meal or vegetable protein can be reduced by adopting the teaching of the present invention resulting in significant cost savings. This is because the relative cost of cereals is significantly less than that of conventional protein supplements. In view of this, a feed can be prepared according to the teaching of the present invention having the same nutritional value in terms of available energy, amino acids and protein as a conventional feed but which includes a higher relative proportion of cereal and a lower relative proportion of protein supplements. It is also found that the inclusion of a thermostable xylanase in an animal feed has the effect that reduced levels of energy supplements such as fats and oils need to be included in order to achieve a feed having a certain level of performance.

The inclusion of a thermostable xylanase in an animal feed in accordance with the present invention enables the crude protein value and/or digestibility and/or the amino acid content and/or digestibility coefficients of the feed to be increased, which permits a reduction in the amounts of alternative protein sources and/or amino acids supplements which have previously had to be included in animal feeds.

When the protein digestibility coefficient and/or the content of available crude protein of wheat is increased by the addition of the thermostable xylanase, major savings can be found in the reduced levels of protein and/or energy supplements which have conventionally needed to be added. Alternatively, when only the amino acid content or digestibility coefficient values are increased by the addition of the thermostable xylanase, the major savings are to be found in the reduced levels of amino acid supplements which have conventionally needed to be added to the feeds.

The feed provided by the present invention may also include other enzyme supplements such as one or more of β-glucanase, glucoamylase, mannanase, α-galactosidase, phytase, lipase, α-arabinofuranosidase, protease, α-amylase and pectinase. It is particularly preferred to include a protease as a further enzyme supplement such as a subtilisin derived from the genus Bacillus. Such subtilisins are for example described in detail in U.S. Pat. No. 4,760,025.

A suitable feed in accordance with the present invention can be obtained by preparing a feed additive comprising a physiologically acceptable carrier and the thermostable xylanase, and then mixing this additive in amounts of 0.01–50 g per kilo with the other components constituting the animal feed (including the cereal and other sources of protein supplement), more preferably 0.1–10 g/kg and most preferably about 1 g/kg.

The present invention will now be further explained by way of the following Reference Examples.

REFERENCE EXAMPLE 1

Purification of Five Xylanases Produced by *Microtetraspora flexuosa*

Xylanase Assays

The presence of xylanase was determined using a remazol brilliant blue dyed birchwood xylan (RBB-xylan) substrate (Megazyme, Australia is the commercial supplier of the substrate.) 200 µl samples are mixed with 250 µl of substrate solution (2% [w/v] RBB-xylan in 50 mM sodium citrate pH 6.5) and incubated at 37° C. for 10 minutes. Undigested xylan is precipitated by the addition of 1 ml 95% ethanol and removed by centrifugation. Released dye remaining in solution is quantified by spectrophotometry ($OD_{590}$) versus ethanol as a blank and is proportional to xylanase activity. Activity may be quantified using a standard curve and is reported as XAU/ml (xylanase activity units per milliliter).

A gel overlay method for detecting the presence of multiple xylanases and to determine their isoelectric points (pI) was also developed using RBB-xylan substrate. Isoelectric focusing (IEF) gels (pH gradient 3–9) are overlaid with a melted agarose/substrate suspension (4% [w/v] agarose, 7 mg/ml RBB-xylan, 0.5% [v/v] glycerol in 50 mM sodium citrate pH 6.5) and incubated at 37° C. After ca. 1 hour xylanase activity is evident as clearing zones. Gels are allowed to dry completely and may be stored. Xylanase pI is determined by comparison with identically run IEF gels containing silver stained pI standards.

Sample

A cell free supernatant of a *Microtetraspora flexuosa* ATCC 35864 fermentation broth (ca. 14 XAU/ml) was concentrated 5× using ultrafiltration (Amicon stir-cell, 350 ml, PM-10 membrane). All samples were filter sterilised. Protein concentration was 12.5 mg/ml by a BCA method (Pierce). Gel overlay analysis determined the presence of five xylanases, pI 8.5, 7.5, 6.2, 5.8, and 5.3. These five xylanases are referred throughout the present specification as xylanases 1–5, respectively.

Purification Methods

A combination of ion exchange chromatography (IEC) and hydrophobic interaction chromatography (IEC and HIC, respectively) were used to purify all five xylanases as follows:

Purification of Xylanases 1 and 2

As a first step, IEC was used to purify xylanases 1 and 2. Concentrated sample was dialysed completely against 10 mM tris-HCl, pH 9.0 (buffer A). 50 ml were applied to a standard chromatography column (Pharmacia C 16/40) packed with 72 ml Q-Sepharose HP (Pharmacia) equilibrated with buffer A at 1 ml/min using a Pharmacia FPLC system. The column was washed with 50 ml of buffer A, then eluted with a 400 ml linear increasing salt gradient, buffer A to 0.25 M NaCl in buffer A. The column was washed of remaining bound protein with 2 M NaCl in buffer A. 10 ml fractions were collected and assayed as previously described.

Xylanases 1 and 2 co-eluted from the column with the initial flow through while the vast remainder of protein was bound by the column. (Xylanases 1 and 2 represent the unbound column fractions).

Hydrophobic interaction chromatography (HIC) was used as a second step to purify and isolate xylanases 1 and 2. Active fractions were pooled and brought to a final ammonium sulfate concentration of 0.2 M by the addition of 2 M ammonium sulfate. 50 mM sodium citrate pH 6.5 was added to a final concentration of 10 mM and the material (ca. 100 ml) was applied to a standard chromatography column (Pharmacia C 16/20) packed with 36 ml Phenyl Sepharose CL-4B (Pharmacia) equilibrated with 0.2 M ammonium sulphate-10 mM sodium citrate pH 6.5 (buffer B) at 0.5 ml/min. The column was washed with 60 ml buffer B, then eluted by stepping the salt concentration down to 10 mM sodium citrate pH 6.5 (buffer C) for 70 ml, stepping down to 10% (v/v) ethylene glycol (EG) in buffer C for 50 ml, applying a 200 ml linear gradient 10–32% EG, washing at 32% EG for 80 ml, applying a 150 ml gradient 32–38% EG and finally stepping up to 50% EG for 70 ml to completely wash the column. 10 ml fractions were collected and assayed as above. Under these conditions, homogeneous xylanase 2 elutes with the 32% EG wash while homogeneous xylanase 1 elutes at the tail end of the 32–38% EG gradient.

Purification of Xylanase 4

Using the above described first step (IEC) for the purification of xylanases 1 and 2, xylanases 4 and 5 co-elute at ca. 0.16 M NaCl in buffer A. Active fractions were pooled and brought to 0.4 M ammonium sulfate-10 mM sodium citrate pH 6.5 (buffer D) as above. Material, ca. 100 ml, was applied at 1 ml/min to above described HIC column which had been equilibrated with buffer D. The column was washed with 50 ml buffer D, eluted with 130 ml linear gradient buffer D to buffer C followed immediately by a 200 ml linear gradient buffer C to 50% EG. 10 ml fractions were collected and assayed as above. Xylanase 4 elutes at ca. 20% EG.

Purification of Xylanases 3 and 5

In the case of xylanases 3 and 5, HIC was used as a first step. Concentrated sample was brought to 0.5 M ammonium sulfate in buffer C by the addition of 2 M ammonium sulfate and 50 mM sodium citrate pH 6.5 (as above). Material was filtered to remove any trace precipitates and a 50 ml volume was applied at 1 ml/min to the above described HIC column which had been equilibrated with 0.5 M ammonium sulfate in buffer C (buffer E). The column was next washed with 87.5 ml buffer E then eluted with a 147 ml linear gradient buffer E to buffer C. 10 ml fractions were collected and assayed as above. Xylanases 3 and 5 co-eluted at ca. 0.05 ammonium sulfate.

IEC was used to isolate and purify xylanases 3 and 5. Active HIC fractions were pooled (70 ml), dialysed completely against 10 mM tris-HCl pH 8.0 (buffer F) and concentrated to ca. 20 ml by above method. Material was applied at 1 ml/min to the above described IEC column which had been equilibrated with buffer F. The column was washed with 150 ml buffer F and eluted with a 150 ml linear gradient buffer F to 0.25 M NaCl in buffer F. 10 ml fractions were collected and assayed as above. Xylanase 3 eluted at ca. 0.05 M NaCl while xylanase 5 eluted at ca. 0.15 M NaCl.

REFERENCE EXAMPLE 2

Characterisation of Five Xylanases Produced by *Microtetraspora flexuosa*

After purification, each xylanase was subjected to isoelectric focusing and a molecular weight determination according to the following procedures. The results of the biochemical characterisation of the xylanases are listed in Table 1.

Isoelectric focusing techniques were carried out using a PhastSystem (Pharmacia Biotech) as per manufacturer's instructions. Markers used for pI determination were a broad pI kit pH 3.5–9.3 (Pharmacia Biotech). Visualisation of proteins was by PhastSystem development silver staining, as per instructions.

Molecular weight determinations were accomplished by two methods: sodium dodecyl sulfate polyacrylamide gel electrophoresis (SDS-PAGE) and mass spectroscopy (MS) SDS-PAGE and subsequent visualisation by silver staining was carried out using a Phast system, as above. Molecular weight markers used were from Sigma Chemical Co. (St. Louis, Mo.). Mass spectroscopy was performed by Charles Evans and Associates (301 Chesapeake Drive, Redwood City, Calif. 94063).

TABLE 1

*Microtetraspora flexuosa* XYLANASES

| No | pI | MW (kD) - method | pH Optimum | pH Stability | Temperature Optimum (° C.) | Stability half-life at 80° C. (min) |
|---|---|---|---|---|---|---|
| 1 | 8.5 | 33.1-MS | 7.0–7.5 | 6–8.5 | 70 | 110 |
| 2 | 7.5 | 13.3-MS | 7.0–7.5 | 6–8 | 65 | 55 |
| 3 | 6.2 | 31.0-SDS | 7.5 | 6–9 | 65 | 30 |
| 4 | 5.8 | 50.0-SDS | 7.5 | 6–9 | 65 | 90 |
| 5 | 5.3 | 35.0-SDS | 7.5 | 6–9 | 70 | 30 |

The pH optimum is determined by using the RBB assay described previously except that the buffers vary depending on the pH ranges measured, i.e., pH 4.5–12.0. (See FIG. 1) It is within the skilled artisan's ability to prepare the appropriate buffer for the selected pH of the assay.

The temperature stability represents the time at a given temperature where half the activity remains. The activity is measured at approximately 18–37° C. A sample is incubated at a given temperature and the activity is measured using the RBB assay. The half life is the time in minutes where half the activity is lost. (See FIG. 3).

The temperature optimum is the temperature where the highest activity is found. FIG. 2 shows the temperature profile of xylanases 1–5 measured using the RBB assay. In both FIGS. 1 and 2, the % maximum activity is related to the highest activity measurement which is given the value 100% and all other numbers are measured relative to that standardisation.

EXAMPLE 1

Xylanases 1–5 from *Microtetraspora flexuosa*, xylanase TfxA from *Thermomonospora fusca*, and xylanases obtained from *Trichoderma viride* and *Aspergillus niger* were tested to determine their relative ability to reduce the viscosity of a wheat arabinoxylan substrate in accordance with the viscosity reducing assay described in detail above. For each of the enzyme compositions, the viscosity was determined without heat treatment (control) and after respective heat treatments for 1 minute and 5 minutes in a water bath set at 95° C. The results of these experiments are summarised in Table 2.

TABLE 2

| Xylanase | Control (no heat treatment) | Viscosity (Pa · s) 20 minutes (at 40° C.) after exposure to 95° C. for: | |
|---|---|---|---|
| | | 1 minute | 5 minutes |
| Xylanases 1–5 from *M. flexuosa* | $1.8 \times 10^{-3}$ | $1.8 \times 10^{-3}$ | $8.8 \times 10^{-3}$ |
| Xylanase TfxA from *T. fusca* | $7.9 \times 10^{-3}$ | $8.2 \times 10^{-3}$ | $1.6 \times 10^{-2}$ |
| Xylanase from *T. viride* | $2.0 \times 10^{-3}$ | $1.1 \times 10^{-2}$ | $1.1 \times 10^{-2}$ |
| Xylanase from *A. niger* | $1.4 \times 10^{-3}$ | $7.2 \times 10^{-3}$ | $7.3 \times 10^{-3}$ |

It can be seen from the above results that exposure of all of the xylanases or mixture of xylanases to a temperature of 95° C. for five minutes significantly reduced xylanase activity as measured by the viscosity-reduction assay. However, it has also to be noted that the viscosity measured for the first xylanase after exposure to 95° C. for one minute was not significantly different from the control, and within the range ±0.001 Pa.s. It is clear on the other hand that the xylanases obtained from *T. viride* and *A. niger* are very much more sensitive to heat compared to the thermostable xylanases used in the present invention.

EXAMPLE 2

The thermostability of the individual xylanases 1 and 2 obtained from *Microtetraspora flexuosa* were assayed according to the viscosity-reducing assay used in Example 1. In common with Example 1, a control run for each xylanase was carried out which was not subjected to any heat treatment. Again, two heat treatments were carried out according to which the enzymes were heated for one minute and five minutes in a water bath set at 95° C. The results of this experiment are summarised in Table 3.

TABLE 3

| Enzyme | Control (no heat treatment) | Viscosity (Pa · s) after exposure to 95° C. for: | |
|---|---|---|---|
| | | 1 minute | 5 minutes |
| xylanase 1 | $1.7 \times 10^{-3}$ | $1.9 \times 10^{-3}$ | $2.4 \times 10^{-3}$ |
| xylanase 2 | $1.7 \times 10^{-3}$ | $2.3 \times 10^{-3}$ | $2.5 \times 10^{-3}$ |

It can be seen from the results set out in Table 3 that the viscosity measured for both xylanase 1 and xylanase 2 after exposure to 95° C. for one minute is within 0.00006 Pa.s of the control viscosity. Accordingly, it is evident that the activity of these two xylanases is not substantially diminished by the heat treatment at 95° C. for 1 minute.

What is claimed is:

1. An enzyme feed additive comprising a physiologically acceptable carrier and one or more xylanases obtained from *Microtetraspora flexuosa* and possessing one or more of the following sets of characteristics (i)–(v):
   (i) a molecular weight of about 33,100 daltons, a pI of about 8.5, and having a maximum activity at a pH in the range 7.0–7.5 and at a temperature of about 70° C.;
   (ii) a molecular weight of about 13,300 daltons, a pI of about 7.5, and having a maximum activity at a pH in the range 7.0–7.5 and at a temperature of about 65° C.;
   (iii) a molecular weight of about 31,000 daltons, a pI of about 6.2, and having a maximum activity at a pH of about 7.5 and at a temperature of about 65° C.;
   (iv) a molecular weight of about 50,000 daltons, a pI of about 5.8, and having a maximum activity at a pH of about 7.5 and at a temperature of about 65° C.;
   (v) a molecular weight of about 35,000 daltons, a pI of about 5.3, and having a maximum activity at a pH of about 7.5 and at a temperature of about 70° C.

2. An enzyme feed additive according to claim 1, wherein the carrier is a cereal or is derived from a cereal.

3. An enzyme feed additive according to claim 2, wherein the carrier is milled wheat, maize, soya or a byproduct of any thereof.

4. A cereal-based feed comprising at least 20% by weight of cereal and 0.00001–10 g of thermostable xylanase protein per kilogram of feed, the thermostable xylanase comprising one or more xylanases obtained from *Microtetraspora flexuosa* and possessing one or more of the following sets of characteristics (i)–(v):
   (i) a molecular weight of about 33,100 daltons, a pI of about 8.5, and having a maximum activity at a pH in the range 7.0–7.5 and at a temperature of about 70° C.;
   (ii) a molecular weight of about 13,300 daltons, a pI of about 7.5, and having a maximum activity at a pH in the range 7.0–7.5 and at a temperature of about 65° C.;
   (iii) a molecular weight of about 31,000 daltons, a pI of about 6.2, and having a maximum activity at a pH of about 7.5 and at a temperature of about 65° C.;
   (iv) a molecular weight of about 50,000 daltons, a pI of about 5.8, and having a maximum activity at a pH of about 7.5 and at a temperature of about 65° C.;
   (v) a molecular weight of about 35,000 daltons, a pI of about 5.3, and having a maximum activity at a pH of about 7.5 and at a temperature of about 70° C.

5. A cereal-based feed according to claim 4 wherein the cereal is at least one of wheat, barley, maize, sorghum, rye, oats, triticale and rice.

6. A method of increasing the feed conversion ratio comprising
   (a) providing a cereal-based feed; and
   (b) adding to the cereal-based feed an enzyme feed additive comprising a physiologically acceptable carrier and one or more xylanases obtained from *Microtetraspora flexuosa* and possessing one or more of the following characteristics (i)–(v):
      (i) a molecular weight of about 33,100 daltons, a pI of about 8.5, and having a maximum activity at a pH in the range 7.0–7.5 and at a temperature of about 70° C.;
      (ii) a molecular weight of about 13,300 daltons, a pI of about 7.5, and having a maximum activity at a pH in the range 7.0–7.5 and at a temperature of about 65° C.;

(iii) a molecular weight of about 31,000 daltons, a pI of about 6.2, and having a maximum activity at a pH of about 7.5 and at a temperature of about 65° C.;

(iv) a molecular weight of about 50,000 daltons, a pI of about 5.8, and having a maximum activity at a pH of about 7.5 and at a temperature of about 65° C.; and (v) a molecular weight of about 35,000 daltons, a pI of about 5.3, and having a maximum activity at a pH of about7.5 and at a temperature of about 70° C.

7. A method of preparing an animal feed for poultry or pigs comprising providing a cereal-based feed comprising at least 20% by weight of cereal and providing 0.00001–10 g of thermostable xylanase protein per kilogram of feed, the thermostable xylanase comprising one or more xylanases obtained from *Microtetraspora flexuosa* and possessing one or more of the following characteristics (i)–(v):

(i) a molecular weight of about 33,100 daltons, a pI of about 8.5, and having a maximum activity at a pH in the range 7.0–7.5 and at a temperature of about 70° C.;

(ii) a molecular weight of about 13,300 daltons, a pI of about 7.5, and having a maximum activity at a pH in the range 7.0–7.5 and at a temperature of about 65° C.;

(iii) a molecular weight of about 31,000 daltons, a pI of about 6.2, and having a maximum activity at a pH of about 7.5 and at a temperature of about 65° C.;

(iv) a molecular weight of about 50,000 daltons, a pI of about 5.8, and having a maximum activity at a pH of about 7.5 and at a temperature of about 65° C.; and (v) a molecular weight of about 35,000 daltons, a pI of about 5.3, and having a maximum activity at a pH of about 7.5 and at a temperature of about 70° C.

* * * * *